(12) United States Patent
Duplessis et al.

(10) Patent No.: US 11,708,354 B2
(45) Date of Patent: Jul. 25, 2023

(54) 2-BENZOPYRAZINYL-N-HETEROARYL-2-PHENYL-ACETAMIDE COMPOUNDS

(71) Applicant: Hoffmann-La Roche Inc., Little Falls, NJ (US)

(72) Inventors: Martin Duplessis, Somerville, MA (US); Georg Jaeschke, Basel (CH); Bernd Kuhn, Reinach BL (CH); Kiel Lazarski, Boston, MA (US); Yanke Liang, Belmont, MA (US); Yvonne Alice Nagel, Basel (CH); Antonio Ricci, Biel-Benken (CH); Daniel Rueher, Raedersdorf (FR); Sandra Steiner, Sursee (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 305 days.

(21) Appl. No.: 17/103,648

(22) Filed: Nov. 24, 2020

(65) Prior Publication Data

US 2021/0070739 A1 Mar. 11, 2021

Related U.S. Application Data

(60) Division of application No. 16/449,040, filed on Jun. 21, 2019, now Pat. No. 10,882,848, which is a continuation of application No. PCT/EP2017/083969, filed on Dec. 21, 2017.

(30) Foreign Application Priority Data

Dec. 22, 2016 (EP) .................... 16206394

(51) Int. Cl.
| | | |
|---|---|---|
| *C07D 403/12* | (2006.01) |
| *C07D 403/14* | (2006.01) |
| *C07D 401/12* | (2006.01) |
| *C07D 401/14* | (2006.01) |
| *C07D 417/12* | (2006.01) |
| *C07D 417/14* | (2006.01) |
| *A61P 35/00* | (2006.01) |
| *A61K 9/48* | (2006.01) |
| *A61K 9/20* | (2006.01) |
| *A61K 9/02* | (2006.01) |
| *A61K 9/00* | (2006.01) |

(52) U.S. Cl.
CPC ............ *C07D 403/12* (2013.01); *A61K 9/009* (2013.01); *A61K 9/0019* (2013.01); *A61K 9/02* (2013.01); *A61K 9/2013* (2013.01); *A61K 9/2018* (2013.01); *A61K 9/2054* (2013.01); *A61K 9/485* (2013.01); *A61K 9/4825* (2013.01); *A61K 9/4858* (2013.01); *A61K 9/4866* (2013.01); *A61K 9/4875* (2013.01); *A61P 35/00* (2018.01); *C07D 401/12* (2013.01); *C07D 401/14* (2013.01); *C07D 403/14* (2013.01); *C07D 417/12* (2013.01); *C07D 417/14* (2013.01)

(58) Field of Classification Search
CPC .. C07D 403/12; C07D 403/14; C07D 401/12; C07D 401/14; A61P 35/00; A61K 9/00; A61K 9/02; A61K 9/20; A61K 9/48
See application file for complete search history.

(56) References Cited

FOREIGN PATENT DOCUMENTS

| | | | |
|---|---|---|---|
| CN | 102060848 A | 5/2011 |
| CN | 102093339 A | 6/2011 |
| WO | 2007/143434 A2 | 12/2007 |
| WO | WO 2007/143434 | * 12/2007 |
| WO | WO 2017/004383 | 1/2017 |

OTHER PUBLICATIONS

U.S. Pat. No. 10,882,848, B2, U.S. Appl. No. 16/449,040, Duplessis et al, Jan. 5, 2021.
U.S. Pat. No. 11,117,890, B2, U.S. Appl. No. 16/700,900, Jaeschke et al, Sep. 14, 2021.
US, 2021/0079005, A1, U.S. Appl. No. 17/105,060, Duplessis et al, Mar. 18, 2021.
Ciardiello, F., and Tortora, G., "EGFR antagonists in cancer treatment", The New England Journal of Medicine, 2008, 358, 1160-1174.
International Preliminary Report on Patentability received for PCT Patent Application No. PCT/EP2017/083969, dated Jul. 4, 2019, 8 pages.
International Search Report and Written Opinion received for PCT Patent Application No. PCT/EP2017/083969, dated Feb. 26, 2018, 10 pages.
Li H Q et al., "Synthesis and structure-activity relationships of N-benzyl-N-(X-2-hydroxybenzyl)-N-phenylureas and thioureas as antitumor agents", Bioorganic and Medicinal Chemistry, 2010, 18(1), 305-313, XP026810721.
Paez, J. et al., "EGFR mutations in lung cancer: correlation with clinical response to gefitinib therapy", Science, 2004, (New York, NY 304, 1497-1500.
Sharma SV, Bell DW, Settleman J, Haber DA., "Epidermal growth factor receptor mutations in lung cancer", Nat Rev Cancer, Mar. 2007;7(3): 169-81.
Thress et al., Acquired EGFR C797S mutation mediates resistance to AZD9291 in non-small cell lung cancer harboring EGFR T790M; Nature Medicine vol. 21 (6) Jun. 2015. published online May 4, 2015; doi:10.1038/nm.3854.
Yarden, Y., Sliwkowski, MX., "Untangling the ErbB signaling network", Nature Review Mol. Cell Biol., 2001, 2(2), 127-37.
Yong Jia et al: "Overcoming EGFR(T790M) 1-20 and EGFR(C797S) resistance with mutant-selective allosteric inhibitors", Nature, vol. 534, No. 7605, May 25, 2016 (May 25, 2016), pp. 129-132.
Huan-Qiu Li et al., Bioorganic & Medicinal Chemistry, vol. 18, Issue 1, pp. 305-313, (2010).

* cited by examiner

*Primary Examiner* — Erich A Leeser
(74) *Attorney, Agent, or Firm* — Knowles Intellectual Property Strategies, LLC

(57) ABSTRACT

The present invention provides compounds which are selective allosteric inhibitors of T790M and C797S containing EGFR mutants, their manufacture, pharmaceutical compositions containing them and their use as therapeutically active substances.

16 Claims, No Drawings

2-BENZOPYRAZINYL-N-HETEROARYL-2-PHENYL-ACETAMIDE COMPOUNDS

CROSS-REFERENCE TO RELATED APPLICATIONS

This application is a divisional of U.S. patent application Ser. No. 16/449,040, filed Jun. 21, 2019, which is a continuation of International Application No. PCT/EP2017/083969, filed in the International Patent Cooperation Treaty, European Receiving Office on Dec. 21, 2017, which claims the benefit of European Patent Application 16206394.5, filed Dec. 22, 2016. The entirety of these applications are hereby incorporated by reference herein for all purposes.

FIELD OF THE INVENTION

The present invention provides compounds which are selective allosteric inhibitors of T790M and C797S containing EGFR mutants, their manufacture, pharmaceutical compositions containing them and their use as therapeutically active substances.

BACKGROUND OF THE INVENTION

The HER family receptor tyrosine kinases are mediators of cell growth, differentiation and survival. The receptor family includes four distinct members, i.e., epidermal growth factor receptor (EGFR, ErbB1, or HER1) HER2 (ErbB2), HER3 (ErbB3) and HER4 (ErbB4). Upon ligand binding the receptors form homo and heterodimers and subsequent activation of the intrinsic tyrosine kinase activity leads to receptor auto-phosphorylation and the activation of downstream signaling molecules (Yarden, Y., Sliwkowski, M X. Untangling the ErbB signaling network. Nature Review Mol. Cell Biol. 2001 February; 2(2): 127-37). De-regulation of EGFR by overexpression or mutation has been implicated in many types of human cancer including colorectal, pancreatic, gliomas, head and neck and lung cancer, in particular, non-small cell lung cancer (NSCLC) and several EGFR targeting agents have been developed over the years (Ciardiello, F., and Tortora, G. (2008). EGFR antagonists in cancer treatment. The New England Journal of Medicine 358, 1160-1174). Erlotinib (Tarceva®), a reversible inhibitor of the EGFR tyrosine kinase was approved in numerous countries for the treatment of recurrent NSCLC.

An impressive single agent activity of EGFR tyrosine kinase inhibitors is observed in a subset of NSCLC patients whose tumors harbor somatic kinase domain mutations, whereas clinical benefit in wild-type EGFR patients is greatly diminished (Paez, J. et al. (2004). EGFR mutations in lung cancer: correlation with clinical response to Gefitinib therapy. Science, 1497-1500). The most common somatic mutations of EGFR are exon 19 deletions with delta 746-750 the most prevalent mutation and the exon 21 amino acid substitutions with L858R the most frequent mutation (Sharma S V, Bell D W, Settleman J, Haber D A. Epidermal growth factor receptor mutations in lung cancer. Nat. Rev. Cancer. 2007 March; 7(3): 169-81).

Treatment resistance arises frequently, often due to the secondary T790M mutation within the ATP site of the receptor. Some developed mutant-selective irreversible inhibitors are highly active against the T790M mutant, but their efficacy can be compromised by acquired mutation of C797, that is the cysteine residue with which they form a key covalent bond (Thress, K. S. et al. Acquired EGFR C797S mutation mediates resistance to AZD9291 in non-small cell lung cancer harboring EGFR T790M. Nat. Med. 21, 560-562 (2015)).

As most available EGFR tyrosine kinase inhibitors target the ATP-site of the kinase, there is a need for new therapeutic agents that work differently, for example through targeting drug-resistant EGFR mutants. The wild-type receptor, however, maintains untroubled.

Recent studies suggest that purposefully targeting allosteric sites might lead to mutant-selective inhibitors (Jia et al. Overcoming EGFR(T790M) and EGFR(C797S) resistance with mutant-selective allosteric inhibitors, June 2016, Nature 534, 129-132). There is need in the generation of selective molecules that specifically inhibit T790M and C797S containing EGFR mutants useful for the therapeutic and/or prophylactic treatment of cancer.

SUMMARY OF THE INVENTION

The present invention provides an indazolyl-2-phenyl-acetamide of formula I, or a pharmaceutically acceptable salt thereof,

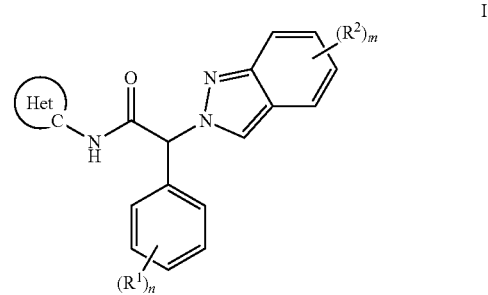

wherein the substituents and variables are as described below and in the claims, or a pharmaceutically acceptable salt thereof.

The present compounds are useful for the therapeutic and/or prophylactic treatment of cancer.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of Alzheimer's disease, cognitive impairment, schizophrenia, pain or sleep disorders.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a," "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. A specific group is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of alkynyl include ethynyl, propynyl, prop-2-ynyl, isopropynyl, n-butynyl, and iso-butynyl. A specific example is ethynyl.

The term "cyano", alone or in combination with other groups, refers to N≡C—(NC—).

The term "amino", alone or in combination with other groups, refers to $NH_2$.

The term "halogen", alone or in combination with other groups, denotes chloro (Cl), iodo (I), fluoro (F) and bromo (Br). A specific group is F.

The term "hydroxy", alone or in combination with other groups, refers to —OH.

The term "heteroaryl", alone or in combination with other groups, refers to an aromatic carbocyclic group having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. The term "5-membered heteroaryl" refers to a single 5-membered aromatic ring, containing 1 or 2 heteroatoms selected from N, O and S, in particular one N and one S, for example thiazolyl. A specific group is thiazol-2-yl. The term "6-membered heteroaryl" refers to a single 6-membered aromatic ring, containing 1 or 2 heteroatoms selected from N, O and S, in particular one N, for example pyridinyl (pyridyl). A specific group is 2-pyridyl. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Specific groups are indazolyl, pyridinyl and thiazolyl.

The term "heterocyclyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl. Specific groups are morpholinyl and piperazinyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. A specific group is methoxy.

The term "halogen-$C_{1-6}$-alkoxy", alone or in combination with other groups, refers to $C_{1-6}$-alkoxy as defined herein, which is substituted by one or multiple halogen, particularly 1-5 halogen, more particularly 1-3 halogen. Particular halogen is fluoro. Particular "halogen-$C_{1-6}$-alkoxy" is fluoro-$C_{1-6}$-alkoxy and a particular "halogen-$C_{1-3}$-alkoxy" is fluoro-$C_{1-3}$-alkoxy. A specific group is —O—$CF_3$.

The term "N-containing heterocyclyl" refers to a monovalent saturated or partly unsaturated mono- or bicyclic ring system of 4 to 9 ring atoms, comprising 1, 2, or 3 ring heteroatoms that are N, the remaining ring atoms being carbon. Bicyclic means consisting of two cycles having two ring atoms in common, i.e. the bridge separating the two rings is either a single bond or a chain of one or two ring atoms. Examples are pyrrolidinyl, piperidinyl and piperazinyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant ($K_i$) using the Cheng-Prusoff equation (Biochem. Pharmacol. (1973) 22:3099).

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

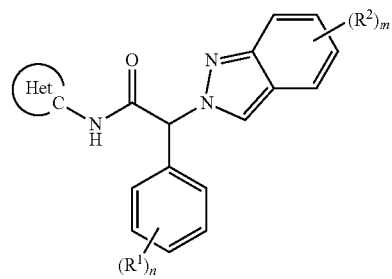

wherein
$R^1$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^2$ is each independently selected from the group consisting of
  i) amino,
  ii) aryl substituted with $(R^3)_k$,
  iii) $C_{1-6}$-alkyl,
  iv) $C_{1-6}$-alkoxy,
  v) $C_{2-6}$-alkynyl substituted with $(R^5)_p$,
  vi) cyano,
  vii) halogen,
  viii) halogen-$C_{1-6}$-alkyl,
  ix) halogen-$C_{1-6}$-alkoxy,
  x) heteroaryl substituted with $(R^4)_l$,
  xi) heterocyclyl substituted with $(R^7)_r$, and
  xii) hydroxy;
$R^3$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^4$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy,
  viii) heterocyclyl substituted with $(R^8)_s$, and
  ix) hydroxy;
$R^5$ is independently selected from the group consisting of
  i) heteroaryl substituted with $(R^6)_q$, and
  ii) $C_{1-6}$-alkyl;
$R^6$ is independently selected from the group consisting of
  i) amino, and
  ii) $C_{1-6}$-alkyl;

$R^7$ is independently selected from the group consisting of
  i) amino, and
  ii) $C_{1-6}$-alkyl;
$R^8$ is independently selected from the group consisting of
  i) amino, and
  ii) $C_{1-6}$-alkyl;
Het is heteroaryl;
k is 0, 1, 2 or 3;
l is 0, 1 or 2;
n is 0, 1, 2 or 3;
m is 0, 1 or 2;
p is 0, 1 or 2;
q is 0, 1 or 2;
r is 0, 1 or 2;
s is 0, 1 or 2;
or a pharmaceutically acceptable salt thereof.

A certain embodiment of the invention relates to the compound of formula I, or a pharmaceutically acceptable salt thereof, as described herein, wherein
$R^1$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^2$ is each independently selected from the group consisting of
  i) amino,
  ii) aryl substituted with $(R^3)_k$,
  iii) $C_{1-6}$-alkyl,
  iv) $C_{1-6}$-alkoxy,
  v) cyano,
  vi) halogen,
  vii) halogen-$C_{1-6}$-alkyl,
  viii) halogen-$C_{1-6}$-alkoxy,
  ix) heteroaryl with $(R^4)_l$, and
  x) hydroxy;
$R^3$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^4$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^5$ is each independently selected from the group consisting of
  i) hydrogen and,
  ii) $C_{1-6}$-alkyl;
Het is a heteroaryl;
k is 0, 1, 2 or 3;
l is 0, 1 or 2;
n is 0, 1, 2 or 3;
m is 0, 1 or 2;
or a pharmaceutically acceptable salt thereof.

A certain embodiment of the invention relates to the compound of formula I, or a pharmaceutically acceptable salt thereof, as described herein, wherein
$R^1$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^2$ is each independently selected from the group consisting of
  i) amino,
  ii) aryl substituted with $(R^3)_k$,
  iii) $C_{1-6}$-alkyl,
  iv) $C_{1-6}$-alkoxy,
  v) cyano,
  vi) halogen,
  vii) halogen-$C_{1-6}$-alkyl,
  viii) halogen-$C_{1-6}$-alkoxy,
  ix) heteroaryl with $(R^4)_l$, and
  x) hydroxy;
$R^3$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^4$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
Het is a heteroaryl;
k is 0, 1, 2 or 3;
l is 0, 1 or 2;
n is 0, 1, 2 or 3;
m is 0, 1 or 2;
or a pharmaceutically acceptable salt thereof.

A certain embodiment of the invention relates to the compound of formula I, or a pharmaceutically acceptable salt thereof, as described herein, wherein m is 2, and one $R^2$ is aryl substituted with $(R^3)_k$ or heteroaryl substituted with $(R^4)_l$, and the other $R^2$ is selected from the group consisting of
  i) amino,
  ii) aryl substituted with $(R^3)_k$,
  iii) $C_{1-6}$-alkyl,
  iv) $C_{1-6}$-alkoxy,
  v) $C_{2-6}$-alkynyl substituted with $(R^5)_p$,
  vi) cyano, vii) halogen,
viii) halogen-$C_{1-6}$-alkyl,
ix) halogen-$C_{1-6}$-alkoxy,
x) heteroaryl substituted with $(R^4)_l$,
xi) heterocyclyl substituted with $(R^7)_r$ and
xii) hydroxy;
and $R^3$, $R^4$, $R^5$, $R^7$, k, l, t and r are as defined herein.

A certain embodiment of the invention relates to the compound of formula I, or a pharmaceutically acceptable salt thereof, as described herein, wherein m is 2, and one $R^2$ is aryl substituted with $(R^3)_k$ or heteroaryl substituted with $(R^4)_l$, and the other $R^2$ is selected from the group consisting of
i) amino,
ii) $C_{1-6}$-alkyl,
iii) $C_{1-6}$-alkoxy,
iv) cyano,
v) halogen,
vi) halogen-$C_{1-6}$-alkyl,
vii) halogen-$C_{1-6}$-alkoxy, and
viii) hydroxy;
and $R^3$, $R^4$, k and l are as defined herein.

A certain embodiment of the invention relates to the compound of formula I, or a pharmaceutically acceptable salt thereof, as described herein, that is of formula Ia.

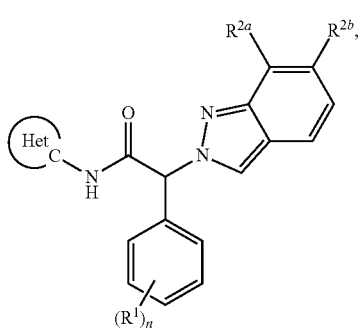

Ia wherein one of $R^{2a}$ and $R^{2b}$ is aryl substituted with $(R^3)_k$ or heteroaryl substituted with $(R^4)_l$, and the other one is selected from the group consisting of
i) amino,
ii) $C_{1-6}$-alkyl,
iii) $C_{1-6}$-alkoxy,
iv) cyano,
v) halogen,
vi) halogen-$C_{1-6}$-alkyl,
vii) halogen-$C_{1-6}$-alkoxy, and
viii) hydroxy;
and $R^3$, $R^4$, k and l are as defined herein.

A certain embodiment of the invention relates to the compound of formula I, or a pharmaceutically acceptable salt thereof, as described herein, wherein n is 2.

A certain embodiment of the invention relates to the compound of formula I, or a pharmaceutically acceptable salt thereof, as described herein, wherein one $R^1$ is halogen, in particular F, and the other is hydroxy.

A certain embodiment of the invention relates to the compound of formula I, or a pharmaceutically acceptable salt thereof, as described herein, wherein n is 0.

A certain embodiment of the invention relates to the compound of formula I, or a pharmaceutically acceptable salt thereof, as described herein, wherein $R^2$ is halogen, amino, aryl substituted with $(R^3)_k$, $C_{1-6}$-alkoxy, $C_{2-6}$-alkynyl substituted with $(R^5)_p$, heteroaryl substituted with $(R^4)_l$, heterocyclyl or hydroxy; in particular amino, Br, Cl, ethynyl substituted with $(R^5)_p$, F, hydroxy, morpholinyl, $OCH_3$, phenyl substituted with $(R^3)_{0-1}$ or pyridyl substituted with $(R^4)_l$; more particularly amino, Br, Cl, ethynyl substituted with pyridyl, ethynyl substituted with $C_{1-6}$-alkyl-pyridyl, F, hydroxy, morpholinyl, $OCH_3$, phenyl substituted with piperazinyl, pyridyl substituted piperazinyl or pyridyl substituted $C_{1-6}$-alkyl-piperazinyl.

A certain embodiment of the invention relates to the compound of formula I, or a pharmaceutically acceptable salt thereof, as described herein, wherein $R^2$ is amino, Br, Cl, ethynyl substituted with $(R^5)_p$, F, hydroxy, morpholinyl, $OCH_3$, phenyl substituted with $(R^3)_{0-1}$ or pyridyl substituted with $(R^4)_l$.

A certain embodiment of the invention relates to the compound of formula I, or a pharmaceutically acceptable salt thereof, as described herein, wherein $R^2$ is amino, Br, Cl, ethynyl substituted with pyridyl, ethynyl substituted with $C_{1-6}$-alkyl-pyridyl, F, hydroxy, morpholinyl, $OCH_3$, phenyl substituted with piperazinyl, pyridyl substituted piperazinyl or pyridyl substituted $C_{1-6}$-alkyl-piperazinyl.

A certain embodiment of the invention relates to the compound of formula I, or a pharmaceutically acceptable salt thereof, as described herein, wherein $R^2$ is amino, hydroxy or $C_{1-6}$-alkoxy, in particular amino, hydroxy or methoxy.

A certain embodiment of the invention relates to the compound of formula I, or a pharmaceutically acceptable salt thereof, as described herein, wherein Het is a 5-membered or 6-membered heteroaryl.

A certain embodiment of the invention relates to the compound of formula I, or a pharmaceutically acceptable salt thereof, as described herein, wherein Het is thiazolyl or pyridyl.

A certain embodiment of the invention relates to the compound of formula I, or a pharmaceutically acceptable salt thereof, as described herein, wherein Het is a 5-membered heteroaryl, in particular thiazolyl or thiadiazolyl.

A certain embodiment of the invention relates to the compound of formula I, or a pharmaceutically acceptable salt thereof, as described herein, wherein Het is a 6-membered heteroaryl, in particular pyridyl.

A certain embodiment of the invention relates to the compound of formula I, or a pharmaceutically acceptable salt thereof, as described herein, wherein k is 1 and $R^3$ is phenyl.

A certain embodiment of the invention relates to the compound of formula I, or a pharmaceutically acceptable salt thereof, as described herein, wherein n is 0, 1 or 2; in particular 0 or 2.

A certain embodiment of the invention relates to the compound of formula I, or a pharmaceutically acceptable salt thereof, as described herein, that is selected from the group consisting of
(2RS)-2-(5-Fluoro-2-hydroxy-phenyl)-2-(6-phenylindazol-2-yl)-N-thiazol-2-yl-acetamide,
(2RS)-2-(5-Fluoro-2-hydroxy-phenyl)-2-(7-phenylindazol-2-yl)-N-thiazol-2-yl-acetamide,
(2RS)-2-(5-Fluoro-2-hydroxy-phenyl)-2-indazol-2-yl-N-thiazol-2-yl-acetamide,
(2RS)-2-(6-Bromoindazol-2-yl)-2-(5-fluoro-2-hydroxyphenyl)-N-thiazol-2-yl-acetamide,
(2RS)-2-(7-Bromoindazol-2-yl)-2-(5-fluoro-2-hydroxyphenyl)-N-thiazol-2-yl-acetamide, (2RS)-2-[6-[2-(6-Amino-3-pyridyl)ethynyl]-7-fluoro-indazol-2-yl]-2-(5-fluoro-2-hydroxy-phenyl)-N-(2-pyridyl)acetamide,
(2RS)-2-[6-[2-(6-Amino-3-pyridyl)ethynyl]-7-fluoro-indazol-2-yl]-2-phenyl-N-thiazol-2-yl-acetamide,
(2RS)-2-[6-[6-(4-Ethylpiperazin-1-yl)-3-pyridyl]indazol-2-yl]-2-(3-fluorophenyl)-N-thiazol-2-yl-acetamide,
(2RS)-2-[7-Chloro-6-(6-piperazin-1-yl-3-pyridyl)indazol-2-yl]-2-phenyl-N-thiazol-2-yl-acetamide,
(2RS)-2-[7-Fluoro-6-(4-piperazin-1-ylphenyl)indazol-2-yl]-2-phenyl-N-thiazol-2-yl-acetamide hydrochloride,
(2RS)-2-[7-Fluoro-6-(6-piperazin-1-yl-3-pyridyl)indazol-2-yl]-2-phenyl-N-(2-pyridyl)acetamide,
(2RS)-2-Phenyl-2-[6-(6-piperazin-1-yl-3-pyridyl)indazol-2-yl]-N-thiazol-2-yl-acetamide hydrochloride,
2-(3-fluorophenyl)-2-[6-[2-(3-pyridyl)ethynyl]indazol-2-yl]-N-thiazol-2-yl-acetamide,
2-(6-aminoindazol-2-yl)-2-phenyl-N-thiazol-2-yl-acetamide,
2-(6-hydroxyindazol-2-yl)-2-phenyl-N-thiazol-2-yl-acetamide,
2-(6-methoxyindazol-2-yl)-2-phenyl-N-thiazol-2-yl-acetamide,
2-indazol-2-yl-2-phenyl-N-(2-pyridyl)acetamide,
2-indazol-2-yl-2-phenyl-N-thiazol-2-yl-acetamide,
2RS)-2-(5-Fluoro-2-hydroxy-phenyl)-2-(7-morpholinoindazol-2-yl)-N-thiazol-2-yl-acetamide, and
2RS)-2-[7-Fluoro-6-(6-piperazin-1-yl-3-pyridyl)indazol-2-yl]-2-phenyl-N-thiazol-2-yl-acetamide hydrochloride.

A certain embodiment of the invention relates to the compound of formula I, or a pharmaceutically acceptable salt thereof, as described herein, that is selected from the group consisting of
2-(5-fluoro-2-hydroxy-phenyl)-2-indazol-2-yl-N-thiazol-2-yl-acetamide,
2-indazol-2-yl-2-phenyl-N-(2-pyridyl)acetamide,
2-(6-aminoindazol-2-yl)-2-phenyl-N-thiazol-2-yl-acetamide,
2-(6-methoxyindazol-2-yl)-2-phenyl-N-thiazol-2-yl-acetamide,
2-(6-hydroxyindazol-2-yl)-2-phenyl-N-thiazol-2-yl-acetamide, and
2-indazol-2-yl-2-phenyl-N-thiazol-2-yl-acetamide,
or a pharmaceutically acceptable salt thereof.

A certain embodiment of the invention relates to the compound of formula I as described herein, or a pharmaceutically acceptable salt thereof, for use as therapeutically active substance.

A certain embodiment of the invention relates to the compound of formula I as described herein, or a pharmaceutically acceptable salt thereof, for the use in the therapeutic and/or prophylactic treatment of cancer, in particular non-small-cell lung cancer.

A certain embodiment of the invention relates to the compound of formula I as described herein, or a pharmaceutically acceptable salt thereof, for the use in the therapeutic and/or prophylactic treatment of non-small-cell lung cancer.

A certain embodiment of the invention relates to the compound of formula I as described herein, or a pharmaceutically acceptable salt thereof, for the manufacture of a medicament for the therapeutic and/or prophylactic treatment of cancer, in particular non-small-cell lung cancer.

A certain embodiment of the invention relates to a pharmaceutical composition comprising the compound of formula I as described herein, or a pharmaceutically acceptable salt thereof, and a pharmaceutically acceptable auxiliary substance.

A certain embodiment of the invention relates to a method for the therapeutic and/or prophylactic treatment of cancer, in particular non-small-cell lung cancer by administering the compound of formula I as described herein, or a pharmaceutically acceptable salt thereof, to a patient.

A certain embodiment of the invention relates to the compound of formula I as described herein, or a pharmaceutically acceptable salt thereof, for the use as a medicament in therapeutic and/or prophylactic treatment of a patient with EGFR activating mutations suffering from cancer, in particular non-small-cell lung cancer, comprising determining the EGFR activating mutations status in said patient and then administering the compound of formula I as described herein, or a pharmaceutically acceptable salt thereof, to said patient.

A certain embodiment of the invention relates to the compound of formula I as described herein, or a pharmaceutically acceptable salt thereof, for the use as a medicament in therapeutic and/or prophylactic treatment of a patient with EGFR activating mutations as determined with a Cobas® EGFR Mutation Test v2 suffering from cancer, in particular non-small-cell lung cancer, comprising determining the EGFR activating mutations status in said patient and then administering the compound of formula I as described herein, or a pharmaceutically acceptable salt thereof, to said patient.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the schemes described in the examples. The starting material is commercially available or may be prepared in accordance with known methods.

The preparation of compounds of formula I is further described in more detail in scheme 1 and in examples 1-6.

compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all inter-

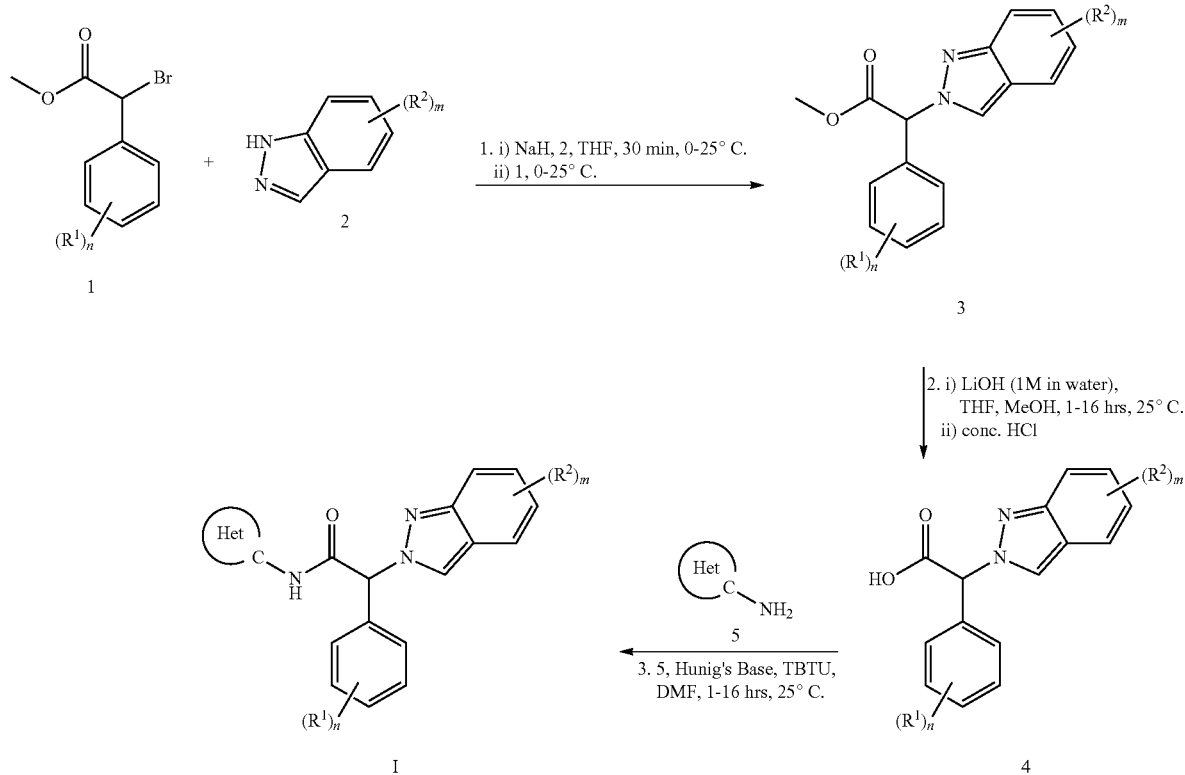

Scheme 1

An indazole based compound of general formula I can be obtained for example by alkylation of an appropriately substituted 1H-indazole 2 with an appropriately substituted bromo-2-phenylacetate 1 to yield the desired ester derivatives of formula 3. Saponifing the ester compounds 3 with a base such as LiOH forms the desired acid derivatives 4. Amide coupling with an appropriately substituted amine of formula 5 with a coupling agent such as TBTU forms the desired indazole based compound of general formula I (scheme 1).

Generally speaking, the sequence of steps used to synthesize the compounds of formula I can also be modified in certain cases.

The corresponding pharmaceutically acceptable salts with acids can be obtained by standard methods known to the person skilled in the art, e.g., by dissolving the compound of formula I in a suitable solvent such as, e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a mediate products can be prepared according to analogous methods or according to the methods set forth herein. Starting materials are commercially available, known in the art or can be prepared by methods known in the art or analogy thereto.

It will be appreciated that the compounds of general formula I in this invention may be derivatized at functional groups to provide derivatives which are capable of conversion back to the parent compound in vivo.

Pharmacological Tests

The compounds of formula I and their pharmaceutically acceptable salts possess valuable pharmacological properties. The compounds were investigated in accordance with the test given hereinafter.

HTRF Phospo EGFR Assay (Cellular)

Cell Line and Media

H1975 cell line was obtained from American Type Culture Collection (Manassas, Va., USA). Cells were maintained at 37° C., 5% $CO_2$ in complete Media RPMI 1640 without phenol red containing 0.3 mg/ml glutamine, 100 IU/ml penicillin, and 100 mg/ml streptomycin (Gibco) supplemented with 10% fetal bovine serum (FBS) (Gibco).

Compounds were diluted into starving medium RPMI 1640 Media without phenol red containing 0.3 mg/ml glutamine, 100 IU/ml penicillin, and 100 mg/ml streptomycin (Gibco).

Protocol

Cells were cultured overnight in a 384-well white plate (8000 cells/well) using 8 µl of complete medium/well. Cells were washed two times with 20 µl of starving medium. Media was removed by tapping plates on tissue and subsequently 8 µl of fresh starving medium/well was added. Then 4 µl/well of the 3× compound solution, containing a half-log dilution series of the compound or DMSO in starving medium, were added to the cells. After 6 hours at 37° C., 5% $CO_2$ cells were lysed by adding to the compound mix 4 µl/well of the supplemented lysis buffer, followed by incubation for 30 min at room temperature with shaking. Lysates were stored at −20° C. over night. The following day plates were thawed and 2 µl of anti-Phospho-EGFR Cryptate and 2 µl of anti-Phospho-EGFR-d2 antibody solutions prepared in the detection buffer were added. The plates were then incubated for at least 4 h at room temperature before reading the fluorescence emission at 620 and 665 nm using PHERAstar FX plate reader (BMG Labtech).

TABLE 1

| Exam. | Structure | $IC_{50}$ [nM] |
|---|---|---|
| 1 | 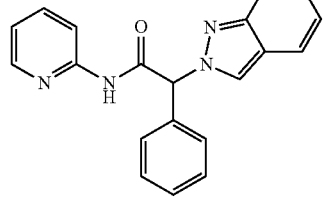 | 1760 |
| 2 | 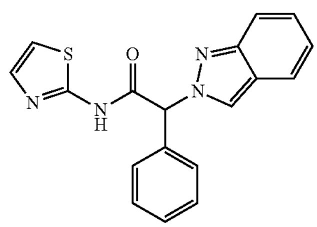 [SMILES: O=C(Nc1nccs1)C(c1ccccc1)n1cc2ccccc2n1] | 77 |
| 3 | 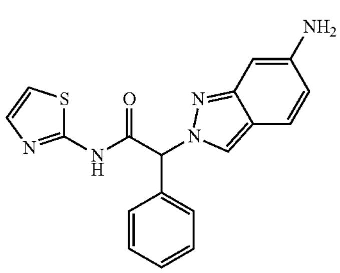 [SMILES: Nc1ccc2cn(C(C(=O)Nc3nccs3)c3ccccc3)nc2c1] | 499 |
| 4 | 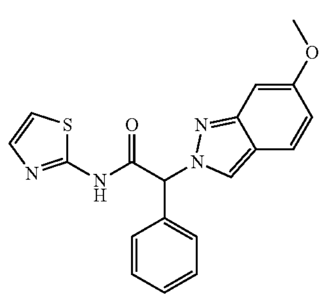 [SMILES: COc1ccc2cn(C(C(=O)Nc3nccs3)c3ccccc3)nc2c1] | 537 |

TABLE 1-continued

| Exam. | Structure | $IC_{50}$ [nM] |
|---|---|---|
| 5 | 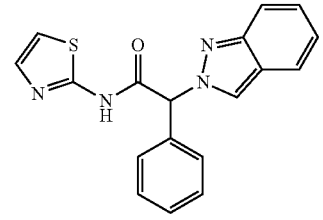 | 199 |
| 6 | 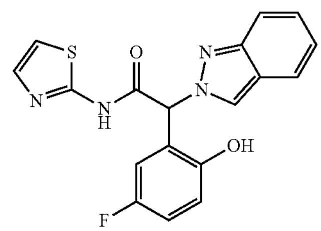 [SMILES: O=C(Nc1nccs1)C(c1cc(F)ccc1O)n1cc2ccccc2n1] | 57 |
| 7 | 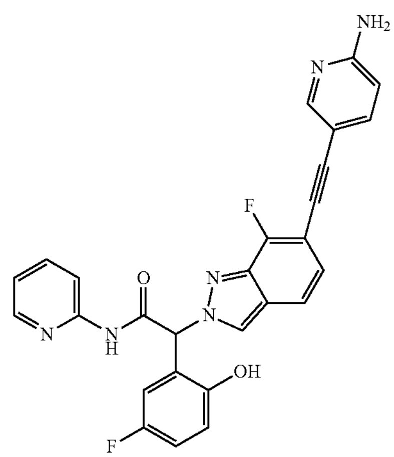 [SMILES: Nc1ccc(C#Cc2ccc3cn(C(C(=O)Nc4ccccn4)c4cc(F)ccc4O)nc3c2F)cn1] | 7 |
| 8 | 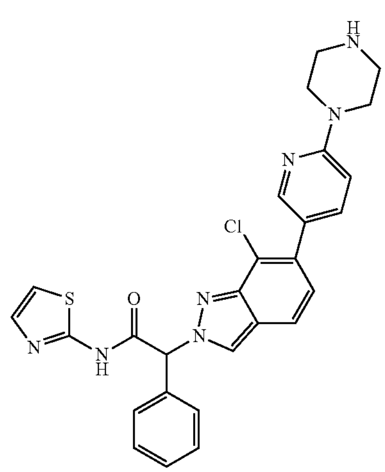 [SMILES: O=C(Nc1nccs1)C(c1ccccc1)n1cc2ccc(-c3ccc(N4CCNCC4)nc3)c(Cl)c2n1] | 32 |

TABLE 1-continued
| Exam. | Structure | IC$_{50}$ [nM] |
|---|---|---|
| 9 | 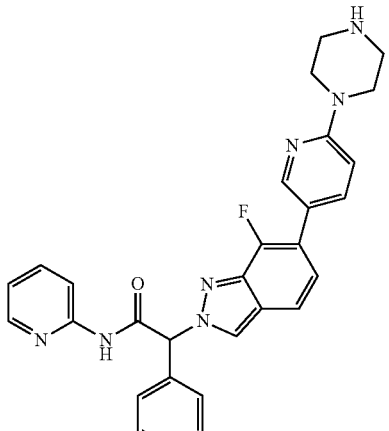 | 127 |
| 10 | 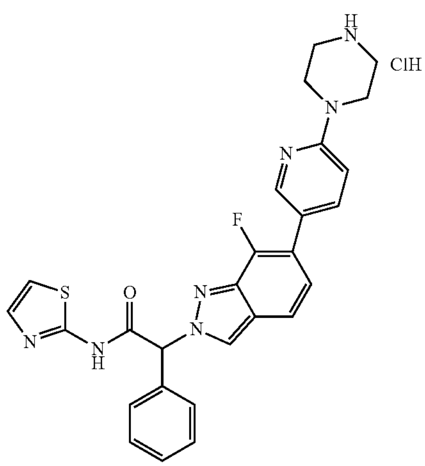 [SMILES: O=C(Nc1nccs1)C(c1ccccc1)n1cc2ccc(-c3ccc(N4CCNCC4)nc3)c(F)c2n1 ; Cl] | 74 |
| 11 | 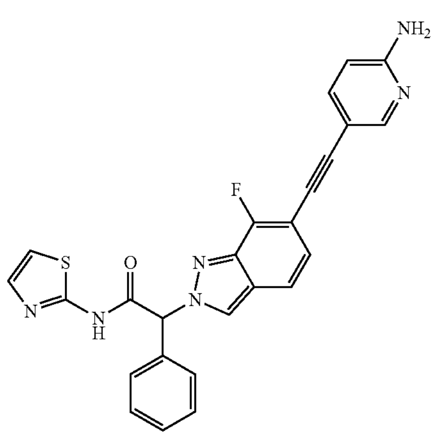 [SMILES: Nc1ccc(C#Cc2ccc3cn(C(C(=O)Nc4nccs4)c4ccccc4)nc3c2F)cn1] | 52 |
| 12 | | 31 |
| 13 | | 144 |
| 14 | | 22 |

TABLE 1-continued

IC$_{50}$ value

| Exam. | Structure | IC$_{50}$ [nM] |
|---|---|---|
| 15 | (structure with Br, thiazole-NH-C(O)-CH(indazole)-phenyl-OH-F) | 1 |
| 16 | (structure with phenyl substituent on indazole) | 55 |
| 17 | (structure with morpholino substituent on indazole) | 60 |
| 18 | (structure with Br on indazole) | 43 |
| 19 | (structure with phenyl on indazole) | 33 |
| 20 | (structure with piperazinyl-pyridinyl substituent on indazole, ClH salt) | 39 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration, the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository molds of suitable size, left to cool; the suppositories are then removed from the molds and packed individually in wax paper or metal foil.

Example D

Injection solutions of the following composition are manufactured:

TABLE 7

| possible injection solution composition | |
| --- | --- |
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
| --- | --- |
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Example 1

(2RS)-2-Indazol-2-yl-2-phenyl-N-(2-pyridyl)acetamide

Step 1: Methyl (2RS)-2-indazol-2-yl-2-phenyl-acetate

Sodium hydride (60% dispersion in mineral oil) (175 mg, 4.37 mmol, 1 equiv.) was suspended in 10 ml of THF and the mixture was cooled to −10 to −15° C. 1H-Indazole (516 mg, 4.37 mmol, 1 equiv.) dissolved in 10 ml of THF was added dropwise at −10° C. to −15° C. The mixture was stirred at room temperature for 30 minutes. Methyl (2RS)-2-bromo-2-phenylacetate (CAS 3042-81-7) (1 g, 4.37 mmol) dissolved in 10 ml of THF was added at −10° C. to −15° C. and the mixture was stirred for 90 minutes at room temperature. The reaction mixture was extracted with water and three times with dichloromethane. The organic layers were dried over sodium sulfate and evaporated to dryness. The crude product was purified by flash chromatography on a silica gel column eluting with an ethyl acetate:heptane 0:100 to 40:60 gradient to obtain the two formed isomers. The desired methyl (2RS)-2-indazol-2-yl-2-phenyl-acetate (146 mg, 13% yield) was obtained as a light yellow solid, MS: m/e=267.2 (M+H$^+$).

Step 2: (2RS)-2-Indazol-2-yl-2-phenyl-acetic acid

Methyl (2RS)-2-indazol-2-yl-2-phenyl-acetate (Example 1, step 1) (146 mg, 0.548 mmol) was dissolved in 1 ml of MeOH and 1 ml of THF and LiOH (1M) (1.1 ml, 1.1 mmol, 2 equiv.) was added. The mixture was stirred for 16 hours at room temperature. The reaction mixture was cooled to 0-5° C. and the pH was adjusted to pH 2 with conc. HCl. The mixture was evaporated to dryness and extracted with brine and three times with ethyl acetate. The organic layers were dried over sodium sulfate and evaporated to dryness. The desired (2RS)-2-indazol-2-yl-2-phenyl-acetic acid (110 mg, 80% yield) was obtained as a white solid, MS: m/e=253.5 (M+H$^+$).

Step 3: (2RS)-2-Indazol-2-yl-2-phenyl-N-(2-pyridyl)acetamide (2RS)-2-Indazol-2-yl-2-phenyl-acetic acid (Example 1, step 2) (50 mg, 0.2 mmol) was dissolved in 1 ml of DMF and pyridin-2-amine (22.4 mg, 0.238 mmol, 1.2 equiv.), Hunig's base (77 mg, 0.1 ml, 0.595 mmol, 3 equiv.) and TBTU (70 mg, 0.218 mmol, 1.1 equiv.) were added at room temperature. The reaction mixture was stirred for 16 hours at room temperature. The reaction mixture was extracted with water and three times with ethyl acetate. The organic layers were extracted with 10% LiCl solution, dried over sodium sulfate and evaporated to dryness. The crude product was purified by flash chromatography on a silica gel column eluting with an ethyl acetate:heptane 0:100 to 70:30 gradient. The desired (2RS)-2-indazol-2-yl-2-phenyl-N-(2-pyridyl)acetamide (25 mg, 38% yield) was obtained as a colorless oil, MS: m/e=329.5 (M+H$^+$).

Example 2

(2RS)-2-Indazol-2-yl-2-phenyl-N-thiazol-2-yl-acetamide

The title compound was obtained as a white solid, MS: m/e=335.0 (M+H$^+$), using chemistry similar to that described in Example 1, step 3 starting from (2RS)-2-indazol-2-yl-2-phenyl-acetic acid (Example 1, step 2) and thiazol-2-amine.

Example 3

(2RS)-2-(6-Aminoindazol-2-yl)-2-phenyl-N-thiazol-2-yl-acetamide

Step 1: Methyl (2RS)-2-(6-nitroindazol-2-yl)-2-phenyl-acetate

The title compound was obtained as a light yellow solid, MS: m/e=312.1 (M+H$^+$), using chemistry similar to that described in Example 1, step 1 starting from methyl (2RS)-2-bromo-2-phenylacetate (CAS 3042-81-7) and 6-nitro-1H-indazole.

Step 2: (2RS)-2-(6-Nitroindazol-2-yl)-2-phenyl-acetic acid

The title compound was obtained as a light yellow solid, MS: m/e=298.0 (M+H$^+$), using chemistry similar to that described in Example 1, step 2 starting from methyl (2RS)-2-(6-nitroindazol-2-yl)-2-phenyl-acetate (Example 3, step 1).

Step 3: (2RS)-2-(6-Nitroindazol-2-yl)-2-phenyl-N-thiazol-2-yl-acetamide

The title compound was obtained as a yellow solid, MS: m/e=380.0 (M+H$^+$), using chemistry similar to that described in Example 1, step 3 starting from (2RS)-2-(6-nitroindazol-2-yl)-2-phenyl-acetic acid (Example 3, step 2) and thiazol-2-amine.

Step 4: (2RS)-2-(6-Aminoindazol-2-yl)-2-phenyl-N-thiazol-2-yl-acetamide (2RS)-2-(6-Nitroindazol-2-yl)-2-phenyl-N-thiazol-2-yl-acetamide (Example 3, step 3) (110 mg, 0.29 mmol) was dissolved in 2 ml of EtOH. Water (100 mg, 5.55 mmol, 20 equiv.), iron (97 mg, 1.74 mmol, 6 equiv.) and ammonium chloride (77 mg, 1.45 mmol, 5 equiv.) were added and the mixture was stirred for 18 hours at 75° C. The reaction mixture was diluted with dichloromethane and the suspension filtered through Celite. The filtrate was extracted with saturated NaHCO$_3$-solution and brine. The organic layer was dried over sodium sulfate and evaporated to dryness. The crude product was purified by flash chromatography on a silica gel column eluting with an ethyl acetate:heptane 0:100 to 60:40 gradient. The desired (2RS)-2-(6-aminoindazol-2-yl)-2-phenyl-N-thiazol-2-yl-acetamide (40 mg, 40% yield) was obtained as a colorless oil, MS: m/e=350.0 (M+H$^+$).

Example 4

(2RS)-2-(6-Methoxyindazol-2-yl)-2-phenyl-N-thiazol-2-yl-acetamide

Step 1: Methyl (2RS)-2-(6-methoxyindazol-2-yl)-2-phenyl-acetate

The title compound was obtained as a brown semi-solid, MS: m/e=297.5 (M+H$^+$), using chemistry similar to that described in Example 1, step 1 starting from methyl (2RS)-2-bromo-2-phenylacetate (CAS 3042-81-7) and 6-methoxy-1H-indazole.

Step 2: (2RS)-2-(6-Methoxyindazol-2-yl)-2-phenyl-acetic acid

The title compound was obtained as a white solid, MS: m/e=283.5 (M+H$^+$), using chemistry similar to that described in Example 1, step 2 starting from methyl (2RS)-2-(6-methoxyindazol-2-yl)-2-phenyl-acetate (Example 4, step 1).

Step 3: (2RS)-2-(6-Methoxyindazol-2-yl)-2-phenyl-N-thiazol-2-yl-acetamide

The title compound was obtained as a white solid, MS: m/e=365.5 (M+H$^+$), using chemistry similar to that described in Example 1, step 3 starting from (2RS)-2-(6-methoxyindazol-2-yl)-2-phenyl-acetic acid (Example 4, step 2) and thiazol-2-amine.

Example 5

(2RS)-2-(6-Hydroxyindazol-2-yl)-2-phenyl-N-thiazol-2-yl-acetamide (2RS)-2-(6-Methoxyindazol-2-yl)-2-phenyl-N-thiazol-2-yl-acetamide (Example 4, step 3) (75 mg, 0.20 mmol) was dissolved in 15 ml of dichloromethane and cooled to 0-5° C. BBr$_3$ (1M in dichloromethane) (0.82 ml, 0.82 mmol, 4 equiv.) was added dropwise and the mixture stirred for 1 hour at room temperature. The mixture was cooled to 0-5° C. and saturated NH4Cl-solution (74 ul, 4.12 mmol, 20 equiv.) was added dropwise. The mixture was stirred for 10 minutes and evaporated with Isolute® to dryness. The crude product was purified by flash chromatography on a silica gel column eluting with a methanol:dichloromethane 0:100 to 20:80 gradient. The desired (2RS)-2-(6-hydroxyindazol-2-yl)-2-phenyl-N-thiazol-2-yl-acetamide (40 mg, 40% yield) was obtained as a colorless oil, MS: m/e=351.5 (M+H$^+$).

Example 6

(2RS)-2-(5-Fluoro-2-hydroxy-phenyl)-2-indazol-2-yl-N-thiazol-2-yl-acetamide

Step 1: Methyl (2RS)-2-(5-fluoro-2-methoxy-phenyl)-2-indazol-2-yl-acetate

The title compound was obtained as a white powder, MS: m/e=315.1 (M+H$^+$), using chemistry similar to that described in Example 1, step 1 starting from methyl (2RS)-2-bromo-2-(5-fluoro-2-methoxyphenyl)acetate (CAS 1368458-30-3) and 1H-indazole.

Step 2: (2RS)-2-(5-Fluoro-2-methoxyphenyl)-2-(2H-indazol-2-yl)acetic acid

The title compound was obtained as a light yellow oil, MS: m/e=301.1 (M+H$^+$), using chemistry similar to that described in Example 1, step 2 starting from methyl (2RS)-2-(5-fluoro-2-methoxy-phenyl)-2-indazol-2-yl-acetate (Example 6, step 1).

Step 3: (2RS)-2-(5-Fluoro-2-methoxyphenyl)-2-(2H-indazol-2-yl)-N-(thiazol-2-yl)acetamide The title compound was obtained as a white solid, MS: m/e=383.0 (M+H$^+$), using chemistry similar to that described in Example 1, step 3 starting from (2RS)-2-(5-fluoro-2-methoxyphenyl)-2-(2H-indazol-2-yl)acetic acid (Example 6, step 2) and thiazol-2-amine.

Step 4: (2RS)-2-(5-Fluoro-2-hydroxy-phenyl)-2-indazol-2-yl-N-thiazol-2-yl-acetamide The title compound was obtained as a light yellow solid, MS: m/e=369.0 (M+H$^+$), using chemistry similar to that described in Example 5 starting from (2RS)-2-(5-fluoro-2-methoxyphenyl)-2-(2H-indazol-2-yl)-N-(thiazol-2-yl)acetamide (Example 6, step 3).

Example 7

(2RS)-2-[6-[2-(6-Amino-3-pyridyl)ethynyl]-7-fluoro-indazol-2-yl]-2-(5-fluoro-2-hydroxy-phenyl)-N-(2-pyridyl)acetamide

Step 1: Methyl (2RS)-2-(6-bromo-7-fluoro-indazol-2-yl)-2-(5-fluoro-2-methoxy-phenyl)acetate Methyl (2RS)-2-bromo-2-(5-fluoro-2-methoxyphenyl)acetate (CAS 1368458-30-3) (650 mg, 2.35 mmol) and 6-bromo-7-fluoro-1H-indazole (CAS 1427396-09-5) (514 mg, 2.39 mmol, 1.0 equiv.) were suspended in 13 ml of acetonitrile and cooled to 0-5° C. Cesium carbonate (917 mg, 2.81 mmol, 1.2 equiv.) was added at 0-5° C. The reaction mixture was stirred for 30 minutes at 0-5° C. and at room temperature for 2 hours. The reaction mixture was extracted with ethyl acetate and water. The aqueous layer was back-extracted with ethyl acetate. The organic layers were washed with brine. The organic layers were combined, dried over sodium sulfate, filtered and evaporated to dryness. The crude product was adsorbed on Isolute® and purified by flash chromatography on a silica gel column eluting with an ethyl acetate:heptane 0:100 to 20:80 gradient. The desired methyl (2RS)-2-(6-bromo-7-fluoro-indazol-2-yl)-2-(5-fluoro-2-methoxy-phenyl)acetate (545 mg, 57% yield) was obtained as a light yellow solid, MS: m/e=411.2/413.2 (M+H$^+$).

Step 2: (2RS)-2-(6-Bromo-7-fluoro-indazol-2-yl)-2-(5-fluoro-2-methoxy-phenyl)acetic acid Methyl (2RS)-2-(6-bromo-7-fluoro-indazol-2-yl)-2-(5-fluoro-2-methoxy-phenyl)acetate (Example 7, step 1) (525 mg, 1.28 mmol) was dissolved in 2.4 ml of THF and 2.4 ml of MeOH. Lithium hydroxide monohydrate (182 mg, 4.34 mmol, 3.4 equiv.) was added followed by 2.4 ml of water and the reaction mixture was stirred at room temperature for 60 minutes. The organic solvents were removed under reduced pressure. The aqueous residue was acidified with 5% Citric acid-solution in water and then extracted with ethyl acetate. The aqueous layer was back-extracted with ethyl acetate. The organic layers were washed with water and brine. The organic layers were combined, dried over sodium sulfate, filtered and evaporated to dryness. The desired (2RS)-2-(6-bromo-7-fluoro-indazol-2-yl)-2-(5-fluoro-2-methoxy-phenyl)acetic acid (498 mg, 98% yield) was obtained as an off-white solid. MS: m/e=397.0/399.0 (M+H$^+$).

Step 3: (2RS)-2-(6-Bromo-7-fluoro-indazol-2-yl)-2-(5-fluoro-2-methoxy-phenyl)-N-(2-pyridyl)acetamide The title compound was obtained as a pink foam, MS: m/e=473.1/475.1 (M+H$^+$), using chemistry similar to that described in Example 1, step 3 starting from (2RS)-2-(6-bromo-7-fluoro-indazol-2-yl)-2-(5-fluoro-2-methoxy-phenyl)acetic acid (Example 7, step 2) and pyridin-2-amine.

Step 4: (2RS)-2-[6-[2-(6-Amino-3-pyridyl)ethynyl]-7-fluoro-indazol-2-yl]-2-(5-fluoro-2-methoxy-phenyl)-N-(2-pyridyl)acetamide (2RS)-2-(6-Bromo-7-fluoro-indazol-2-yl)-2-(5-fluoro-2-methoxy-phenyl)-N-(2-pyridyl)acetamide (Example 7, step 3) (250 mg, 0.528 mmol) was dissolved in 4.4 ml of DMF and 5-ethynylpyridin-2-amine (75 mg, 0.635 mmol, 1.2 equiv.), triethylamine (167 mg, 0.23 ml, 1.65 mmol, 3.1 equiv.), triphenylphosphine (14 mg, 0.0534 mmol, 0.10 equiv.), bis(triphenylphosphine)palladium (II) dichloride (19 mg, 0.0271 mmol, 0.05 equiv.) and copper (I) iodide (5.0 mg, 0.0263 mmol, 0.05 equiv.) were added and the reaction mixture was stirred at 80° C. for 16 hours. The reaction mixture was cooled to room temperature 5-ethynylpyridin-2-amine (75 mg, 0.635 mmol, 1.2 equiv.), triethylamine (87.1 mg, 0.12 ml, 0.861 mmol, 1.6 equiv.), triphenylphosphine (14 mg, 0.0534 mmol, 0.10 equiv.), bis(triphenylphosphine)palladium (II) dichloride (19 mg, 0.0271 mmol, 0.05 equiv.) and copper (I) iodide (5.0 mg, 0.0263 mmol, 0.05 equiv.) were added and the reaction mixture was stirred at 100° C. for 4 hours. The reaction mixture was extracted with ethyl acetate and water. The aqueous layer was back-extracted twice with ethyl acetate. The organic layers were washed three times with water and once with brine. The organic layers were combined, dried over sodium sulfate, filtered and evaporated to dryness. The crude product was adsorbed on Isolute® and purified by flash chromatography on a silica gel column eluting with dichloromethane:methanol 100:0 to 95:5 gradient to obtain the desired (2RS)-2-[6-[2-(6-amino-3-pyridyl)ethynyl]-7-fluoro-indazol-2-yl]-2-(5-fluoro-2-methoxy-phenyl)-N-(2-pyridyl)acetamide as a light brown foam, MS: m/e=511.2 (M+H$^+$).

Step 5: (2RS)-2-[6-[2-(6-Amino-3-pyridyl)ethynyl]-7-fluoro-indazol-2-yl]-2-(5-fluoro-2-hydroxy-phenyl)-N-(2-pyridyl)acetamide The title compound was obtained as a yellow solid, MS: m/e=497.2 (M+H$^+$), using chemistry similar to that described in Example 5 starting from (2RS)-2-[6-[2-(6-amino-3-pyridyl)ethynyl]-7-fluoro-indazol-2-yl]-2-(5-fluoro-2-methoxy-phenyl)-N-(2-pyridyl)acetamide (Example 7, step 4).

Example 8

(2RS)-2-[7-Chloro-6-(6-piperazin-1-yl-3-pyridyl)indazol-2-yl]-2-phenyl-N-thiazol-2-yl-acetamide

Step 1: 6-Bromo-7-chloro-1H-indazole

To a solution of 4-bromo-3-chloro-2-fluorobenzaldehyde (CAS 1696224-75-5) (10.4 g, 43.8 mmol) in 200 ml of 1-butanol was added hydrazine hydrate (11.19 g, 218.99 mmol, 5 equiv.) at room temperature. The reaction mixture was stirred at 120° C. for 36 hours. The reaction mixture was extracted with ethyl acetate and 1 M aqueous HCl. The organic layer was washed with brine, dried over sodium sulfate and evaporated to dryness. The crude product was purified by trituration with dichloromethane. The desired 6-bromo-7-chloro-1H-indazole (3.9 g, 36% yield) was obtained as a yellow solid, MS: m/e=230.9/232.9 (M+H$^+$).

Step 2: Methyl (2RS)-2-(6-bromo-7-chloro-indazol-2-yl)-2-phenyl-acetate

The title compound was obtained as a light yellow oil, MS: m/e=379.0/381.0 (M+H$^+$), using chemistry similar to that described in Example 7, step 1 starting from 6-bromo-7-chloro-1H-indazole (Example 8, step 1) and methyl (2RS)-2-bromo-2-phenylacetate (CAS 3042-81-7) and using potassium carbonate instead of cesium carbonate and stirring the reaction mixture at 65° C. for 15 hours.

Step 3: (2RS)-2-(6-Bromo-7-chloro-indazol-2-yl)-2-phenyl-acetic acid

The title compound was obtained as a white solid, MS: m/e=365.0/367.0 (M+H$^+$), using chemistry similar to that described in Example 1, step 2 starting from methyl (2RS)-2-(6-bromo-7-chloro-indazol-2-yl)-2-phenyl-acetate (Example 8, step 2).

Step 4: (2RS)-2-(6-Bromo-7-chloro-indazol-2-yl)-2-phenyl-N-thiazol-2-yl-acetamide The title compound was obtained as a light yellow solid, MS: m/e=447.0/449.0 (M+H$^+$), using chemistry similar to that described in Example 1, step 3 starting from (2RS)-2-(6-bromo-7-chloro-indazol-2-yl)-2-phenyl-acetic acid (Example 8, step 3) and thiazol-2-amine.

Step 5: tert-Butyl 4-[5-[7-chloro-2-[(1RS)-2-oxo-1-phenyl-2-(thiazol-2-ylamino)ethyl]indazol-6-yl]-2-pyridyl]piperazine-1-carboxylate (2RS)-2-(6-Bromo-7-chloro-indazol-2-yl)-2-phenyl-N-thiazol-2-yl-acetamide (Example 8, step 4) (438 mg, 0.959 mmol) and (6-(4-(tert-butoxycarbonyl)piperazin-1-yl)pyridin-3-yl)boronic acid (CAS 919347-67-4) (353 mg, 1.15 mmol, 1.2 equiv.) were dissolved in 6.0 ml of dioxane, 2.0 ml of water and 2 M aq. Na$_2$CO$_3$-solution (1.44 ml, 2.88 mmol, 3 equiv.). Dichloro[1,1'-bis(diphenylphosphino)ferrocene]-palladium(II), complex with dichloromethane (54.8 mg, 0.0671 mmol, 0.07 equiv.) was added and the reaction mixture was stirred at 90° C. for 25 hours. The reaction mixture was cooled to room temperature and then extracted with ethyl acetate and saturated NaHCO$_3$-solution. The aqueous layer was back-extracted with ethyl acetate. The organic layers were washed with water and brine. The organic layers were combined, dried over sodium sulfate, filtered and evaporated to dryness. The crude product was purified by flash chromatography on a silica gel column eluting with an ethyl acetate:heptane 0:100 to 100:0 gradient. The desired tert-butyl 4-[5-[7-chloro-2-[(1RS)-2-oxo-1-phenyl-2-(thiazol-2-ylamino)ethyl]indazol-6-yl]-2-pyridyl]piperazine-1-carboxylate (128 mg, 21% yield) was obtained as a light yellow foam, MS: m/e=630.4/632.4 (M+H$^+$).

Step 6: (2RS)-2-[7-Chloro-6-(6-piperazin-1-yl-3-pyridyl)indazol-2-yl]-2-phenyl-N-thiazol-2-yl-acetamide tert-Butyl 4-[5-[7-chloro-2-[(1RS)-2-oxo-1-phenyl-2-(thiazol-2-ylamino)ethyl]indazol-6-yl]-2-pyridyl]piperazine-1-carboxylate (Example 8, step 5) (110 mg, 0.175 mmol) was dissolved in 1 ml of dichloromethane and 1 ml of methanol. HCl (4 M in dioxane) (0.44 ml, 1.75 mmol, 10 equiv.) was added at room temperature and the reaction mixture was stirred at room temperature for 16 hours. The reaction mixture was evaporated to dryness. The crude material was basified with saturated NaHCO$_3$-solution and extracted three times with dichloromethane. The organic layers were combined, dried over sodium sulfate, filtered and evaporated to dryness. The desired (2RS)-2-[7-chloro-6-(6-piperazin-1-yl-3-pyridyl)indazol-2-yl]-2-phenyl-N-thiazol-2-yl-acet-amide (60 mg, 65% yield) was obtained as a light yellow foam, MS: m/e=530.2/532.2 (M+H$^+$).

Example 9

(2RS)-2-[7-Fluoro-6-(6-piperazin-1-yl-3-pyridyl)indazol-2-yl]-2-phenyl-N-(2-pyridyl)acetamide Step 1: Methyl (2RS)-2-(6-bromo-7-fluoro-indazol-2-yl)-2-phenyl-acetate The title compound was obtained as a light yellow oil, MS: m/e=362.9/364.9 (M+H$^+$), using chemistry similar to that described in Example 1, step 1 starting from methyl (2RS)-2-bromo-2-phenylacetate (CAS 3042-81-7) and 6-bromo-7-fluoro-1H-indazole (CAS 1427396-09-5).

Step 2: (2RS)-2-(6-Bromo-7-fluoro-indazol-2-yl)-2-phenyl-acetic acid

The title compound was obtained as a light yellow solid, MS: m/e=348.9/350.9 (M+H$^+$), using chemistry similar to that described in Example 7, step 2 starting from methyl (2RS)-2-(6-bromo-7-fluoro-indazol-2-yl)-2-phenyl-acetate (Example 9, step 1).

Step 3: (2RS)-2-(6-Bromo-7-fluoro-indazol-2-yl)-2-phenyl-N-(2-pyridyl)acetamide

The title compound was obtained as a light pink solid, MS: m/e=425.0/426.7 (M+H$^+$), using chemistry similar to that described in Example 1, step 3 starting from (2RS)-2-(6-bromo-7-fluoro-indazol-2-yl)-2-phenyl-acetic acid (Example 9, step 2) and pyridin-2-amine.

Step 4: tert-Butyl 4-[5-[7-fluoro-2-[(1RS)-2-oxo-1-phenyl-2-(2-pyridylamino)ethyl]indazol-6-yl]-2-pyridyl]piperazine-1-carboxylate The title compound was obtained as an off-white foam, MS: m/e=608.3 (M+H$^+$), using chemistry similar to that described in Example 8, step 5 starting from (2RS)-2-(6-bromo-7-fluoro-indazol-2-yl)-2-phenyl-N-(2-pyridyl)acetamide (Example 9, step 3) and (6-(4-(tert-butoxycarbonyl)piperazin-1-yl)pyridin-3-yl)boronic acid (CAS 919347-67-4).

Step 5: (2RS)-2-[7-Fluoro-6-(6-piperazin-1-yl-3-pyridyl)indazol-2-yl]-2-phenyl-N-(2-pyridyl)acetamide The title compound was obtained as an off-white foam, MS: m/e=508.3 (M+H$^+$), using chemistry similar to that described in Example 8, step 6 starting from tert-butyl 4-[5-[7-fluoro-2-[(1RS)-2-oxo-1-phenyl-2-(2-pyridylamino)ethyl]indazol-6-yl]-2-pyridyl]piperazine-1-carboxylate (Example 9, step 4).

Example 10

(2RS)-2-[7-Fluoro-6-(4-piperazin-1-ylphenyl)indazol-2-yl]-2-phenyl-N-thiazol-2-yl-acetamide hydrochloride Step 1: (2RS)-2-(6-Bromo-7-fluoro-indazol-2-yl)-2-phenyl-N-thiazol-2-yl-acetamide The title compound was obtained as a light yellow solid, MS: m/e=430.8/432.8 (M+H$^+$), using chemistry similar to that described in Example 1, step 3 starting from (2RS)-2-(6-bromo-7-fluoro-indazol-2-yl)-2-phenyl-acetic acid (Example 9, step 2) and thiazol-2-amine.

Step 2: tert-Butyl 4-[4-[7-fluoro-2-[(1RS)-2-oxo-1-phenyl-2-(thiazol-2-ylamino)ethyl]indazol-6-yl]phenyl]piperazine-1-carboxylate A screw-capped vial was charged with (2RS)-2-(6-bromo-7-fluoro-indazol-2-yl)-2-phenyl-N-thiazol-2-yl-acetamide (Example 10, step 1) (0.110 g, 0.255 mmol), (4-(4-(tert-butoxycarbonyl)piperazin-1-yl)phenyl)boronic acid (CAS 457613-78-4) (94 mg, 0.307 mmol, 1.2 equiv.), sodium carbonate (108 mg, 1.02 mmol, 4.0 equiv.), tetrakis(triphenylphosphine)palladium (0) (45 mg, 0.0389 mmol, 0.153 equiv.), 2.4 ml of 1,2-dimethoxyethane and 0.40 ml of water. The vial was flushed with argon and stirred at 90° C. for 16 hours. Tetrakis(triphenylphosphine)palladium (0) (30 mg, 0.026 mmol, 0.102 equiv.) was added and the reaction mixture was stirred at 100° C. for 7 hours. The reaction mixture was cooled to room temperature and then extracted with ethyl acetate and saturated NaHCO$_3$-solution. The aqueous layer was back-extracted with ethyl acetate. The organic layers were combined, dried over sodium sulfate, filtered and evaporated to dryness. The crude product was purified by flash chromatography on a silica gel column eluting with an ethyl acetate:heptane 0:100 to 50:0 gradient. The desired tert-butyl 4-[4-[7-fluoro-2-[(1RS)-2-oxo-1-phenyl-2-(thiazol-2-ylamino)ethyl]indazol-6-yl]phenyl]piperazine-1-carboxylate (20 mg, 12% yield) was obtained as a light yellow solid, MS: m/e=613.1 (M+H$^+$)

Step 3: (2RS)-2-[7-Fluoro-6-(4-piperazin-1-ylphenyl)indazol-2-yl]-2-phenyl-N-thiazol-2-yl-acetamide hydrochloride tert-Butyl 4-[4-[7-fluoro-2-[(1RS)-2-oxo-1-phenyl-2-(thiazol-2-ylamino)ethyl]indazol-6-yl]phenyl]piperazine-1-carboxylate (Example 10, step 2) (15 mg, 0.0245 mmol) was dissolved in 0.20 ml of dichloromethane and 0.10 ml of methanol. HCl (4 M in dioxane) (0.070 ml, 0.280 mmol, 11.4 equiv.) was added at room temperature and the reaction mixture was stirred at room temperature for 16 hours. The reaction mixture was evaporated to dryness. The crude product was purified by trituration with dichloromethane. The desired (2RS)-2-[7-fluoro-6-(4-piperazin-1-ylphenyl)indazol-2-yl]-2-phenyl-N-thiazol-2-yl-acetamide hydrochloride (14 mg, 99% yield) was obtained as a yellow solid, MS: m/e=513.2 (M+H$^+$)

Example 11

(2RS)-2-[6-[2-(6-Amino-3-pyridyl)ethynyl]-7-fluoro-indazol-2-yl]-2-phenyl-N-thiazol-2-yl-acetamide The title compound was obtained as a light yellow oil, MS: m/e=469.0 (M+H$^+$), using chemistry similar to that described in Example 7, step 4 starting from (2RS)-2-(6-bromo-7-fluoro-indazol-2-yl)-2-phenyl-N-thiazol-2-yl-acetamide (Example 10, step 1) and 5-ethynylpyridin-2-amine.

Example 12

(2RS)-2-[7-Fluoro-6-(6-piperazin-1-yl-3-pyridyl)indazol-2-yl]-2-phenyl-N-thiazol-2-yl-acetamide hydrochloride

Step 1: tert-Butyl 4-[5-[7-fluoro-2-[(1RS)-2-oxo-1-phenyl-2-(thiazol-2-ylamino)ethyl]indazol-6-yl]-2-pyridyl]piperazine-1-carboxylate The title compound was obtained as an off-white foam, MS: m/e=614.7 (M+H$^+$), using chemistry similar to that described in Example 10, step 2 starting from (2RS)-2-(6-bromo-7-fluoro-indazol-2-yl)-2-phenyl-N-thiazol-2-yl-acetamide (Example 10, step 1) and (6-(4-(tert-butoxycarbonyl)piperazin-1-yl)pyridin-3-yl)boronic acid (CAS 919347-67-4).

Step 2: (2RS)-2-[7-Fluoro-6-(6-piperazin-1-yl-3-pyridyl)indazol-2-yl]-2-phenyl-N-thiazol-2-yl-acetamide hydrochloride The title compound was obtained as an off-white solid, MS: m/e=514.1 (M+H$^+$), using chemistry similar to that described in Example 10, step 3 starting from tert-Butyl 4-[5-[7-fluoro-2-[(1RS)-2-oxo-1-phenyl-2-(thiazol-2-ylamino)ethyl]indazol-6-yl]-2-pyridyl]piperazine-1-carboxylate (Example 12, step 1).

Example 13

(2RS)-2-[6-[6-(4-Ethylpiperazin-1-yl)-3-pyridyl]indazol-2-yl]-2-(3-fluorophenyl)-N-thiazol-2-yl-acetamide

Step 1: Methyl (2RS)-2-(3-fluorophenyl)-2-(6-iodoindazol-2-yl)acetate

The title compound was obtained as an orange oil, MS: m/e=410.0 (M+H$^+$), using chemistry similar to that described in Example 1, step 1 starting from methyl (2RS)-2-bromo-2-(3-fluorophenyl)acetate (CAS 503541-03-5) and 6-iodo-1H-indazole (CAS 261953-36-0).

Step 2: (2RS)-2-(3-Fluorophenyl)-2-(6-iodoindazol-2-yl)acetic acid

Methyl (2RS)-2-(3-fluorophenyl)-2-(6-iodoindazol-2-yl)acetate (Example 13, step 1) (1.23 g, 3 mmol) was dissolved in 6 ml of MeOH and 18 ml of THF. NaOH (1M) (6 ml, 6 mmol, 2 equiv.) was added under ice-bath cooling at room temperature and the mixture was stirred for 2 hours at room temperature. The reaction mixture was poured into KHSO4-solution (1M) and extracted twice with a mixture of dichloromethane/methanol (9:1). The organic layers were dried over sodium sulfate and evaporated to dryness. The desired (2RS)-2-(3-fluorophenyl)-2-(6-iodoindazol-2-yl)acetic acid (1.23 g, quant. yield) was obtained as an off-white foam, MS: m/e=397.4 (M+H$^+$).

Step 3: (2RS)-2-(3-Fluorophenyl)-2-(6-iodoindazol-2-yl)-N-thiazol-2-yl-acetamide The title compound was obtained as a light yellow foam, MS: m/e=479.4 (M+H$^+$), using chemistry similar to that described in Example 1, step 3 starting from (2RS)-2-(3- fluorophenyl)-2-(6-iodoindazol-2-yl)acetic acid (Example 13, step 2) and thiazol-2-amine.

Step 4: tert-Butyl 4-[5-[2-[(1RS)-1-(3-fluorophenyl)-2-oxo-2-(thiazol-2-ylamino)ethyl]indazol-6-yl]-2-pyridyl]piperazine-1-carboxylate The title compound was obtained as a white foam, MS: m/e=614.7 (M+H$^+$), using chemistry similar to that described in Example 8, step 5 starting from (2RS)-2-(3-fluorophenyl)-2-(6-iodoindazol-2-yl)-N-thiazol-2-yl-acetamide (Example 13, step 3) and (6-(4-(tert-butoxycarbonyl)piperazin-1-yl)pyridin-3-yl)boronic acid (CAS 919347-67-4).

Step 5: (2RS)-2-(3-Fluorophenyl)-2-[6-(6-piperazin-1-yl-3-pyridyl)indazol-2-yl]-N-thiazol-2-yl-acetamide hydrochloride tert-Butyl 4-[5-[2-[(1RS)-1-(3-fluorophenyl)-2-oxo-2-(thiazol-2-ylamino)ethyl]indazol-6-yl]-2-pyridyl]piperazine-1-carboxylate (Example 13, step 4) (56 mg, 0.0912 mmol) was dissolved in 5 ml of methanol. HCl (4 M in dioxane) (0.228 ml, 0.912 mmol, 10 equiv.) was added at room temperature and the reaction mixture was stirred at room temperature for 16 hours. The reaction mixture was evaporated to dryness. The desired (2RS)-2-(3-fluorophenyl)-2-[6-(6-piperazin-1-yl-3-pyridyl)indazol-2-yl]-N-thiazol-2-yl-acetamide hydrochloride (62 mg, quant. yield) was obtained as a white foam, MS: m/e=514.6 (M+H$^+$)

Step 6: (2RS)-2-[6-[6-(4-Ethylpiperazin-1-yl)-3-pyridyl]indazol-2-yl]-2-(3-fluorophenyl)-N-thiazol-2-yl-acetamide (2RS)-2-(3-Fluorophenyl)-2-[6-(6-piperazin-1-yl-3-pyridyl)indazol-2-yl]-N-thiazol-2-yl-acetamide hydrochloride (Example 13, step 5) (28 mg, 0.0477 mmol) and iodoethane (8.93 mg, 0.00458 ml, 0.0573 mmol, 1.2 equiv.) were dissolved in 2 ml of DMF and Hunig's base (49.4 mg, 0.0667 ml, 0.382 mmol, 8 equiv.). The reaction mixture was stirred at 60° C. for 2 hours. Iodoethane (8.93 mg, 0.00458 ml, 0.0573 mmol, 1.2 equiv.) was added and the reaction mixture was stirred at 60° C. for 16 hours. Iodoethane (8.93 mg, 0.00458 ml, 0.0573 mmol, 1.2 equiv.) was added and the reaction mixture was stirred at 60° C. for 1 hour. The mixture was evaporated to dryness. The crude product was purified by flash chromatography on a silica gel column eluting with a methanol:dichloromethane 0:100 to 20:80 gradient. The desired (2RS)-2-[6-[6-(4-ethylpiperazin-1-yl)-3-pyridyl]indazol-2-yl]-2-(3-fluorophenyl)-N-thiazol-2-yl-acetamide (10 mg, 39% yield) was obtained as a yellow foam, MS: m/e=542.6 (M+H$^+$)

Example 14

(2RS)-2-(3-Fluorophenyl)-2-[6-[2-(3-pyridyl)ethynyl]indazol-2-yl]-N-thiazol-2-yl-acetamide The title compound was obtained as an off-white foam, MS: m/e=454.5 (M+H$^+$), using chemistry similar to that described in Example 7, step 4 starting from (2RS)-2-(3-fluorophenyl)-2-(6-iodoindazol-2-yl)-N-thiazol-2-yl-acetamide (Example 13, step 3) and 3-ethynylpyridine (CAS 2510-23-8) and using THF as a solvent instead of DMF.

Example 15

(2RS)-2-(7-Bromoindazol-2-yl)-2-(5-fluoro-2-hydroxy-phenyl)-N-thiazol-2-yl-acetamide Step 1: Methyl (2RS)-2-(7-bromoindazol-2-yl)-2-(5-fluoro-2-methoxy-phenyl)acetate The title compound was obtained as an off-white foam, MS: m/e=393.0/395.0 (M+H$^+$), using chemistry similar to that described in Example 1, step 1 starting from methyl (2RS)-2-bromo-2-(5-fluoro-2-methoxyphenyl)acetate (CAS 1368458-30-3) and 7-bromo-1H-indazole (CAS 53857-58-2).

Step 2: (2RS)-2-(7-Bromoindazol-2-yl)-2-(5-fluoro-2-methoxy-phenyl)acetic acid

The title compound was obtained as an off-white solid, MS: m/e=379.4/381.4 (M+H$^+$), using chemistry similar to that described in Example 13, step 2 starting from methyl (2RS)-2-(7-bromoindazol-2-yl)-2-(5-fluoro-2-methoxy-phenyl)acetate (Example 15, step 1).

Step 3: (2RS)-2-(7-Bromoindazol-2-yl)-2-(5-fluoro-2-methoxy-phenyl)-N-thiazol-2-yl-acetamide The title compound was obtained as an off-white foam, MS: m/e=461.5/463.5 (M+H$^+$), using chemistry similar to that described in Example 1, step 3 starting from (2RS)-2-(7-bromoindazol-2-yl)-2-(5-fluoro-2-methoxy-phenyl)acetic acid (Example 15, step 2) and thiazol-2-amine.

Step 4: (2RS)-2-(7-Bromoindazol-2-yl)-2-(5-fluoro-2-hydroxy-phenyl)-N-thiazol-2-yl-acetamide The title compound was obtained as an off-white solid, MS: m/e=447.5/449.5 (M+H$^+$), using chemistry similar to that described in Example 5 starting from (2RS)-2-(7-bromoindazol-2-yl)-2-(5-fluoro-2-methoxy-phenyl)-N-thiazol-2-yl-acetamide (Example 15, step 3).

Example 16

(2RS)-2-(5-Fluoro-2-hydroxy-phenyl)-2-(7-phenylindazol-2-yl)-N-thiazol-2-yl-acetamide Step 1: (2RS)-2-(5-Fluoro-2-methoxy-phenyl)-2-(7-phenylindazol-2-yl)-N-thiazol-2-yl-acetamide A mixture of (2RS)-2-(7-bromoindazol-2-yl)-2-(5-fluoro-2-methoxy-phenyl)-N-thiazol-2-yl-acetamide (Example 15, step 3) (100 mg, 0.217 mmol), 3 ml of dioxane, phenylboronic acid (39.6 mg, 0.325 mmol, 1.5 equiv.), potassium phosphate tribasic (0.5 M) (1.3 ml, 0.650 mmol, 3 equiv.) and Xphos Pd G2 catalyst (CAS 1310584-14-5) (17.1 mg, 0.0217 mmol, 0.1 equiv.) was degassed by argon bubbling for 10 minutes. The reaction vial was sealed and stirred at 100° C. for 4.5 hours. The reaction mixture was cooled to room temperature, poured into saturated NaHCO$_3$-solution and extracted twice with ethyl acetate. The organic layers were washed with brine, combined, dried over sodium sulfate, filtered and evaporated to dryness. The crude product was purified by flash chromatography on a silica gel column eluting with a methanol:dichloromethane 0:100 to 15:85 gradient. The desired (2RS)-2-(5-fluoro-2-methoxyphenyl)-2-(7-phenylindazol-2-yl)-N-thiazol-2-yl-acetamide (42 mg, 42% yield) was obtained as an off-white foam, MS: m/e=459.5 (M+H$^+$)

Step 2: (2RS)-2-(5-Fluoro-2-hydroxy-phenyl)-2-(7-phenylindazol-2-yl)-N-thiazol-2-yl-acetamide The title compound was obtained as a white solid, MS: m/e=445.5 (M+H$^+$), using chemistry similar to that described in Example 5 starting from (2RS)-2-(5-fluoro-2-methoxy-phenyl)-2-(7-phenylindazol-2-yl)-N-thiazol-2-yl-acetamide (Example 16, step 1).

Example 17

(2RS)-2-(5-Fluoro-2-hydroxy-phenyl)-2-(7-morpholinoindazol-2-yl)-N-thiazol-2-yl-acetamide Step 1: (2RS)-2-(5-Fluoro-2-methoxy-phenyl)-2-(7-morpholinoindazol-2-yl)-N-thiazol-2-yl-acetamide A mixture of (2RS)-2-(7-bromoindazol-2-yl)-2-(5-fluoro-2-methoxy-phenyl)-N-thiazol-2-yl-acetamide (Example 15, step 3) (80 mg, 0.173 mmol), 3 ml of dioxane, morpholine (22.7 mg, 0.0224 ml, 0.260 mmol, 1.5 equiv.), potassium tert-butoxide (58.4 mg, 0.520 mmol, 3 equiv.) and Pd-PEPPSI™-IPent catalyst (CAS 1158652-41-5) (13.8 mg, 0.0173 mmol, 0.1 equiv.) was degassed by five times alternating evacuating and backfilling with argon. The reaction mixture was stirred at 100° C. for 1 hour. The reaction mixture was cooled to room temperature, poured into saturated NH4Cl-solution and extracted twice with a mixture of dichloromethane/methanol (9:1). The organic layers were combined, dried over sodium sulfate, filtered and evaporated to dryness. The crude product was purified by flash chromatography on a silica gel column eluting with a methanol: dichloromethane 0:100 to 15:85 gradient. The desired (2RS)-2-(5-fluoro-2-methoxy-phenyl)-2-(7-morpholinoindazol-2-yl)-N-thiazol-2-yl-acetamide (53 mg, 65% yield) was obtained as a light brown foam, MS: m/e=468.6 (M+H$^+$)

Step 2: (2RS)-2-(5-Fluoro-2-hydroxy-phenyl)-2-(7-morpholinoindazol-2-yl)-N-thiazol-2-yl-acetamide The title compound was obtained as an off-white foam, MS: m/e=454.6 (M+H$^+$), using chemistry similar to that described in Example 5 starting from (2RS)-2-(5-fluoro-2-methoxy-phenyl)-2-(7-morpholinoindazol-2-yl)-N-thiazol-2-yl-acetamide (Example 17, step 1).

Example 18

(2RS)-2-(6-Bromoindazol-2-yl)-2-(5-fluoro-2-hydroxy-phenyl)-N-thiazol-2-yl-acetamide Step 1: Methyl (2RS)-2-(6-bromoindazol-2-yl)-2-(5-fluoro-2-methoxy-phenyl)acetate The title compound was obtained as a yellow oil, MS: m/e=393.0/395.0 (M+H$^+$), using chemistry similar to that described in Example 1, step 1 starting from methyl (2RS)-2-bromo-2-(5-fluoro-2-methoxyphenyl)acetate (CAS 1368458-30-3) and 6-bromo-1H-indazole (CAS 79762-54-2).

Step 2: (2RS)-2-(6-Bromoindazol-2-yl)-2-(5-fluoro-2-methoxy-phenyl)acetic acid

The title compound was obtained as a light brown foam, MS: m/e=379.0/380.9 (M+H$^+$), using chemistry similar to that described in Example 13, step 2 starting from methyl (2RS)-2-(6-bromoindazol-2-yl)-2-(5-fluoro-2-methoxy-phenyl)acetate (Example 18, step 1).

Step 3: (2RS)-2-(6-Bromoindazol-2-yl)-2-(5-fluoro-2-methoxy-phenyl)-N-thiazol-2-yl-acetamide The title compound was obtained as a yellow solid, MS: m/e=461.0/463.0 (M+H$^+$), using chemistry similar to that described in Example 1, step 3 starting from (2RS)-2-(6-bromoindazol-2-yl)-2-(5-fluoro-2-methoxy-phenyl)acetic acid (Example 18, step 2) and thiazol-2-amine.

Step 4: (2RS)-2-(6-Bromoindazol-2-yl)-2-(5-fluoro-2-hydroxy-phenyl)-N-thiazol-2-yl-acetamide The title compound was obtained as a white solid, MS: m/e=446.9/448.9 (M+H$^+$), using chemistry similar to that described in Example 5 starting from (2RS)-2-(6-bromoindazol-2-yl)-2-(5-fluoro-2-methoxy-phenyl)-N-thiazol-2-yl-acetamide (Example 18, step 3).

Example 19

(2RS)-2-(5-Fluoro-2-hydroxy-phenyl)-2-(6-phenylindazol-2-yl)-N-thiazol-2-yl-acetamide Step 1: (2RS)-2-(5-Fluoro-2-methoxy-phenyl)-2-(6-phenylindazol-2-yl)-N-thiazol-2-yl-acetamide The title compound was obtained as a light brown solid, MS: m/e=459.2 (M+H$^+$), using chemistry similar to that described in Example 16, step 1 starting from (2RS)-2-(6-bromoindazol-2-yl)-2-(5-fluoro-2-methoxy-phenyl)-N-thiazol-2-yl-acetamide (Example 18, step 3) and phenylboronic acid.

Step 2: (2RS)-2-(5-Fluoro-2-hydroxy-phenyl)-2-(6-phenylindazol-2-yl)-N-thiazol-2-yl-acetamide The title compound was obtained as a white solid, MS: m/e=445.2 (M+H$^+$), using chemistry similar to that described in Example 5 starting from (2RS)-2-(5-fluoro-2-methoxy-phenyl)-2-(6-phenylindazol-2-yl)-N-thiazol-2-yl-acetamide (Example 19, step 1).

Example 20

(2RS)-2-Phenyl-2-[6-(6-piperazin-1-yl-3-pyridyl)indazol-2-yl]-N-thiazol-2-yl-acetamide hydrochloride Step 1: Methyl (2RS)-2-(6-iodoindazol-2-yl)-2-phenylacetate The title compound was obtained as an orange oil, MS: m/e=393.4 (M+H$^+$), using chemistry similar to that described in Example 1, step 1 starting from methyl (2RS)-2-bromo-2-phenylacetate (CAS 3042-81-7) and 6-iodo-1H-indazole.

Step 2: (2RS)-2-(6-Iodoindazol-2-yl)-2-phenyl-acetic acid

The title compound was obtained as a light yellow foam, MS: m/e=379.4 (M+H$^+$), using chemistry similar to that described in Example 7, step 2 starting from methyl (2RS)-2-(6-iodoindazol-2-yl)-2-phenyl-acetate (Example 20, step 1).

Step 3: (2RS)-2-(6-Iodoindazol-2-yl)-2-phenyl-N-(2-pyridyl)acetamide

The title compound was obtained as a yellow solid, MS: m/e=461.4 (M+H$^+$), using chemistry similar to that described in Example 1, step 3 starting from (2RS)-2-(6-iodoindazol-2-yl)-2-phenyl-acetic acid (Example 20, step 2) and thiazol-2-amine.

Step 4: tert-Butyl 4-[5-[2-[(1RS)-2-oxo-1-phenyl-2-(thiazol-2-ylamino)ethyl]indazol-6-yl]-2-pyridyl]piperazine-1-carboxylate The title compound was obtained as a white solid, MS: m/e=597.0 (M+H$^+$), using chemistry similar to that described in Example 8, step 5 starting from (2RS)-2-(6-iodoindazol-2-yl)-2-phenyl-N-(2-pyridyl)acetamide (Example 20, step 3) and tert-butyl 4-[5-(4,4,5,5-tetramethyl-1,3,2-dioxaborolan-2-yl)-2-pyridyl]piperazine-1-carboxylate.

Step 5: (2RS)-2-Phenyl-2-[6-(6-piperazin-1-yl-3-pyridyl)indazol-2-yl]-N-thiazol-2-yl-acetamide hydrochloride The title compound was obtained as an white solid, MS: m/e=496.3 (M+H$^+$), using chemistry similar to that described in Example 8, step 6 starting from tert-butyl 4-[5-[2-[(1RS)-2-oxo-1-phenyl-2-(thiazol-2-ylamino)ethyl]indazol-6-yl]-2-pyridyl]piperazine-1-carboxylate (Example 20, step 4).

We claim:

1. A method for the therapeutic treatment of cancer, comprising administering to a patient in need thereof a therapeutically effective amount of a compound of Formula I:

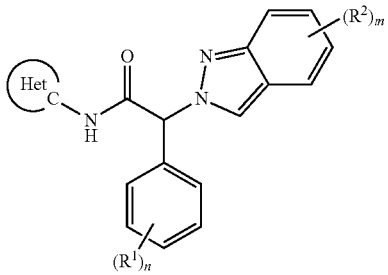

wherein
$R^1$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^2$ is each independently selected from the group consisting of
  i) amino,
  ii) aryl substituted with $(R^3)_k$,
  iii) $C_{1-6}$-alkyl,
  iv) $C_{1-6}$-alkoxy,
  v) $C_{2-6}$-alkynyl substituted with $(R^5)_p$,
  vi) cyano,
  vii) halogen,
  viii) halogen-$C_{1-6}$-alkyl,
  ix) halogen-$C_{1-6}$-alkoxy,
  x) heteroaryl substituted with $(R^4)_l$,
  xi) heterocyclyl substituted with $(R^7)_r$, and
  xii) hydroxy;
$R^3$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^4$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy,
  viii) heterocyclyl substituted with $(R^8)_s$, and
  ix) hydroxy;
$R^5$ is independently selected from the group consisting of
  i) heteroaryl substituted with $(R^6)_q$, and
  ii) $C_{1-6}$-alkyl;
$R^6$ is independently selected from the group consisting of
  i) amino, and
  ii) $C_{1-6}$-alkyl;
$R^7$ is independently selected from the group consisting of
  i) amino, and
  ii) $C_{1-6}$-alkyl;
$R^8$ is independently selected from the group consisting of
  i) amino, and
  ii) $C_{1-6}$-alkyl;
Het is heteroaryl;
k is 0, 1, 2 or 3;
l is 0, 1 or 2;
n is 0, 1, 2 or 3;
m is 0, 1 or 2;
p is 0, 1 or 2;
q is 0, 1 or 2;
r is 0, 1 or 2;
s is 0, 1 or 2;
or a pharmaceutically acceptable salt thereof.

2. The method of claim 1, wherein the patient is a human.

3. The method of claim 2, wherein the cancer is a non-small-cell lung cancer.

4. The method of claim 2, wherein the human has an EGFR activating mutation.

5. The method of claim 4, wherein the cancer is a non-small-cell lung cancer.

6. The method of claim 2, wherein n is 2.

7. The method of claim 6, wherein one $R^1$ is F, and the other is hydroxy.

8. The method of claim 2, wherein n is 0.

9. The method of claim 2, wherein $R^2$ is Br, Cl, ethynyl substituted with $R^5$, F, hydroxy, morpholinyl, $OCH_3$, phenyl substituted with $R^3$ or pyridyl substituted with $R^4$.

10. The method of claim 2, wherein $R^2$ is amino, Br, Cl, ethynyl substituted with pyridyl, ethynyl substituted with $C_{1-6}$-alkyl-pyridyl, F, hydroxy, morpholinyl, $OCH_3$, phenyl substituted with piperazinyl, pyridyl substituted piperazinyl or pyridyl substituted $C_{1-6}$-alkyl-piperazinyl.

11. The method of claim 2, wherein $R^2$ is amino, hydroxy or methoxy.

12. The method of claim 2, wherein Het is a 5-membered or 6-membered heteroaryl.

13. The method of claim 2, wherein Het is thiazolyl.

14. The method of claim 2, wherein Het is pyridyl.

15. The method of claim 2, wherein the compound is selected from the group consisting of
  (2RS)-2-(5-Fluoro-2-hydroxy-phenyl)-2-(6-phenylindazol-2-yl)-N-thiazol-2-yl-acetamide,
  (2RS)-2-(5-Fluoro-2-hydroxy-phenyl)-2-(7-phenylindazol-2-yl)-N-thiazol-2-yl-acetamide,
  (2RS)-2-(5-Fluoro-2-hydroxy-phenyl)-2-indazol-2-yl-N-thiazol-2-yl-acetamide,
  (2RS)-2-(6-Bromoindazol-2-yl)-2-(5-fluoro-2-hydroxyphenyl)-N-thiazol-2-yl-acetamide,
  (2RS)-2-(7-Bromoindazol-2-yl)-2-(5-fluoro-2-hydroxyphenyl)-N-thiazol-2-yl-acetamide,
  (2RS)-2-[6-[2-(6-Amino-3-pyridyl)ethynyl]-7-fluoro-indazol-2-yl]-2-(5-fluoro-2-hydroxy-phenyl)-N-(2-pyridyl)acetamide,
  (2RS)-2-[6-[2-(6-Amino-3-pyridyl)ethynyl]-7-fluoro-indazol-2-yl]-2-phenyl-N-thiazol-2-yl-acetamide,
  (2RS)-2-[6-[6-(4-Ethylpiperazin-1-yl)-3-pyridyl]indazol-2-yl]-2-(3-fluorophenyl)-N-thiazol-2-yl-acetamide,
  (2RS)-2-[7-Chloro-6-(6-piperazin-1-yl-3-pyridyl)indazol-2-yl]-2-phenyl-N-thiazol-2-yl-acetamide,
  (2RS)-2-[7-Fluoro-6-(4-piperazin-1-ylphenyl)indazol-2-yl]-2-phenyl-N-thiazol-2-yl-acetamide hydrochloride,
  (2RS)-2-[7-Fluoro-6-(6-piperazin-1-yl-3-pyridyl)indazol-2-yl]-2-phenyl-N-(2-pyridyl)acetamide,
  (2RS)-2-Phenyl-2-[6-(6-piperazin-1-yl-3-pyridyl)indazol-2-yl]-N-thiazol-2-yl-acetamide hydrochloride,
  2-(3-fluorophenyl)-2-[6-[2-(3-pyridyl)ethynyl]indazol-2-yl]-N-thiazol-2-yl-acetamide,
  2-(6-aminoindazol-2-yl)-2-phenyl-N-thiazol-2-yl-acetamide,
  2-(6-hydroxyindazol-2-yl)-2-phenyl-N-thiazol-2-yl-acetamide,
  2-(6-methoxyindazol-2-yl)-2-phenyl-N-thiazol-2-yl-acetamide,
  2-indazol-2-yl-2-phenyl-N-(2-pyridyl)acetamide,
  2-indazol-2-yl-2-phenyl-N-thiazol-2-yl-acetamide,
  2RS)-2-(5-Fluoro-2-hydroxy-phenyl)-2-(7-morpholinoindazol-2-yl)-N-thiazol-2-yl-acetamide, and
  2RS)-2-[7-Fluoro-6-(6-piperazin-1-yl-3-pyridyl)indazol-2-yl]-2-phenyl-N-thiazol-2-yl-acetamide hydrochloride.

16. The method of claim 2, wherein the compound is selected from the group consisting of
  2-(5-fluoro-2-hydroxy-phenyl)-2-indazol-2-yl-N-thiazol-2-yl-acetamide,
  2-indazol-2-yl-2-phenyl-N-(2-pyridyl)acetamide,
  2-(6-aminoindazol-2-yl)-2-phenyl-N-thiazol-2-yl-acetamide,
  2-(6-methoxyindazol-2-yl)-2-phenyl-N-thiazol-2-yl-acetamide,
  2-(6-hydroxyindazol-2-yl)-2-phenyl-N-thiazol-2-yl-acetamide, and
  2-indazol-2-yl-2-phenyl-N-thiazol-2-yl-acetamide.

* * * * *